(12) United States Patent
Menn

(10) Patent No.: US 11,026,711 B2
(45) Date of Patent: *Jun. 8, 2021

(54) SPECIMEN RETRIEVAL DEVICE INCLUDING AN INTEGRATED SLIDING GRASPER

(71) Applicant: Covidien LP, Mansfield, MA (US)

(72) Inventor: Dmitri Menn, Marblehead, MA (US)

(73) Assignee: Covidien LP, Mansfield, MA (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/972,368

(22) Filed: May 7, 2018

(65) Prior Publication Data

US 2018/0250026 A1     Sep. 6, 2018

Related U.S. Application Data

(63) Continuation of application No. 14/270,658, filed on May 6, 2014, now Pat. No. 9,987,031.

(60) Provisional application No. 61/834,948, filed on Jun. 14, 2013.

(51) Int. Cl.
| | |
|---|---|
| *A61B 17/29* | (2006.01) |
| *A61B 17/00* | (2006.01) |
| *A61B 17/30* | (2006.01) |

(52) U.S. Cl.
CPC ........ *A61B 17/29* (2013.01); *A61B 17/00234* (2013.01); *A61B 2017/00287* (2013.01); *A61B 2017/00349* (2013.01); *A61B 2017/306* (2013.01)

(58) Field of Classification Search
CPC .............. A61B 17/29; A61B 17/00234; A61B 2017/00287; A61B 2017/00349; A61B 2017/306
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| | | (Continued) | |

FOREIGN PATENT DOCUMENTS

| | | |
|---|---|---|
| CA | 2792692 A1 | 4/2013 |
| CN | 102755177 A | 10/2012 |
| | (Continued) | |

OTHER PUBLICATIONS

European Search Report EP 12191639.9 dated Feb. 20, 2013.
(Continued)

*Primary Examiner* — Jing Rui Ou

(57) ABSTRACT

A specimen retrieval device is provided. The specimen retrieval device includes a housing including an outer shaft extending distally therefrom. An inner shaft is disposed within the outer shaft and includes at least one tissue engaging device configured to engage tissue and at least one spring. A pouch is coupled to the inner shaft and the at least one spring. The pouch includes an open proximal end and a closed distal end and is movable from a first configuration for deployment from the outer shaft to a second configuration for receiving tissue therein. The at least one tissue engaging device is positionable within the pouch and movable along the inner shaft for engaging tissue and pulling the tissue within the pouch.

18 Claims, 6 Drawing Sheets

(56) References Cited

U.S. PATENT DOCUMENTS

| | | |
|---|---|---|
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,905,497 B2 | 6/2005 | Truckai et al. |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,670,346 B2 | 3/2010 | Whitfield |
| 7,762,959 B2 | 7/2010 | Bilsbury |
| 7,819,121 B2 | 10/2010 | Amer |
| 7,837,612 B2 | 11/2010 | Gill et al. |
| 8,057,485 B2 | 11/2011 | Hollis et al. |
| 8,579,914 B2 | 11/2013 | Menn et al. |
| 8,906,036 B2 | 12/2014 | Farascioni |
| 9,987,031 B2 | 6/2018 | Menn |
| 2002/0068943 A1 | 6/2002 | Chu et al. |
| 2002/0082516 A1 | 6/2002 | Stefanchik |
| 2002/0137988 A1* | 9/2002 | Shipp ............... A61B 17/00234 600/204 |
| 2003/0055417 A1 | 3/2003 | Truckai |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2004/0225192 A1 | 11/2004 | Young |
| 2004/0242960 A1 | 12/2004 | Orban, III |
| 2005/0085808 A1 | 4/2005 | Nakao |
| 2005/0165411 A1 | 7/2005 | Orban |
| 2005/0267492 A1 | 12/2005 | Poncet et al. |
| 2006/0025781 A1 | 2/2006 | Young et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniftin |

(56) References Cited

U.S. PATENT DOCUMENTS

| | | |
|---|---|---|
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152609 A1 | 6/2010 | Zwolinski et al. |
| 2010/0256522 A1 | 10/2010 | Zhou |
| 2011/0184430 A1 | 7/2011 | Parihar et al. |
| 2011/0184431 A1 | 7/2011 | Parihar et al. |
| 2011/0184434 A1 | 7/2011 | Parihar et al. |
| 2011/0184436 A1 | 7/2011 | Shelton, IV et al. |
| 2011/0190781 A1 | 8/2011 | Collier et al. |
| 2011/0190782 A1 | 8/2011 | Fleming et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0277758 A1 | 11/2012 | Davis |
| 2013/0023895 A1 | 1/2013 | Saleh |
| 2013/0267950 A1 | 10/2013 | Rosa et al. |
| 2013/0325025 A1* | 12/2013 | Hathaway ........ A61B 17/00234 606/114 |

FOREIGN PATENT DOCUMENTS

| | | |
|---|---|---|
| DE | 3542667 A1 | 6/1986 |
| DE | 8435489 U1 | 8/1986 |
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004082462 A2 | 9/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011049918 A1 | 4/2011 |
| WO | 2011090862 A2 | 7/2011 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Nov. 26, 2014 issued in European Application No. 14172314.
European Search Report dated Oct. 22, 2015, issued in European Application No. 15171981.
Chinese Office Action dated Dec. 4, 2017, issued in CN Application No. 2014102678160.

* cited by examiner

SPECIMEN RETRIEVAL DEVICE INCLUDING AN INTEGRATED SLIDING GRASPER

CROSS-REFERENCE TO RELATED APPLICATIONS

This application is a continuation of U.S. patent application Ser. No. 14/270,658 filed on May 6, 2014, now U.S. Pat. No. 9,987,031, which claims the benefit of and priority to U.S. Provisional Patent Application No. 61/834,948, filed Jun. 14, 2013, and the disclosures of each of the above-identified applications are hereby incorporated by reference in their entirety.

BACKGROUND

Technical Field

The present disclosure relates to a specimen retrieval device. More particularly, the present disclosure relates to a specimen retrieval device including an integrated sliding grasper.

Background of Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organs must be removed via the access opening in the skin, or through a cannula. Various types of entrapment devices are known in the art to facilitate this procedure. Conventional entrapment devices typically include an elongated applicator including a handle at a proximal end that is operable to deploy a pouch or other suitable device from a distal end of the applicator. The pouch, typically, is formed from a thin sheet of material (e.g., nylon) that is impervious to prevent unwanted tissue cell migration.

One of the difficulties that may occur during minimally invasive procedures is when large excised tissue specimens are being positioned within the pouch, e.g., long specimens, into the pouch. For example, placing a relatively long excised specimen into an unsupported pouch using a separate implement (e.g., graspers) may sometimes prove difficult for a surgeon because the pouch may not maintain its unfolded configuration. Further, long excised specimens sometimes tend to "bunch up" when positioned inside the pouch, which may make it difficult to retrieve the pouch through the usually small laparoscopic incision. As can be appreciated, tissue specimen retrieval under such conditions can cause the pouch to rupture, which, in turn, may result in the excised specimen (or portion thereof) migrating out of the pouch.

SUMMARY

As can be appreciated, a specimen retrieval device including an integrated sliding grasper that is provided within a pouch of the specimen retrieval device may prove useful in the surgical arena.

An aspect of the instant disclosure provides a specimen retrieval device. The specimen retrieval device includes a housing that includes an outer shaft extending distally therefrom. An inner shaft is disposed within the outer shaft. The inner shaft includes one or more tissue engaging devices configured to engage tissue and one or more springs. A pouch is coupled to the inner shaft and the at least one spring. The pouch includes an open proximal end and a closed distal end and is movable from a first configuration for deployment from the outer shaft to a second configuration for receiving tissue therein. The tissue engaging device is repositionable within the pouch and movable along the inner shaft for engaging tissue and pulling the tissue into the pouch.

The tissue engaging device may be movable along a rail of the inner shaft. The rail may include a channel configured to allow the tissue engaging device to move along the rail.

The tissue engaging device may be a pair of jaw members, a needle, a barbed suture or a suction device. The specimen retrieval device may include an actuation device that is configured to move the pair of jaw members from an open configuration for grasping tissue to a closed configuration for pulling the tissue within the pouch. Moreover, the actuation device also may be configured to move the pair of jaw members longitudinally along the inner shaft.

The spring may be configured to move the pouch from the first configuration to the second configuration. The specimen retrieval device may include a cinch handle including a cinch that couples to the open proximal end the pouch for cinching the pouch to a cinched configuration. The pouch may taper towards the closed distal end thereof when the pouch is in the second configuration.

An aspect of the instant disclosure provides a specimen retrieval device. The specimen retrieval device includes a housing that includes an outer shaft extending distally therefrom. An inner shaft is disposed within the outer shaft and is deployable therefrom. The inner shaft including one or more channels and one or more springs. The channel has one or more tissue engaging devices positioned therein for longitudinal movement therealong. A pouch is coupled to a distal end of the inner shaft and the spring so as to abut a portion of the channel of the inner shaft. The pouch includes an open proximal end and a closed distal end and is movable via the at least one spring from a first configuration for deployment from the outer shaft to a second configuration for receiving tissue therein. The tissue engaging device is movable within the pouch along the channel for engaging tissue and for pulling tissue into the pouch.

The channel of the inner shaft may be provided on a rail of the inner shaft. The tissue engaging device may be a pair of jaw members or a needle. The specimen retrieval device may include an actuation device that is configured to move the pair of jaw members from an open configuration for grasping tissue to a closed configuration for pulling the tissue into the pouch. Moreover, the actuation device also may be configured to move the pair of jaw members The specimen retrieval device may include a cinch handle including a cinch that couples to the open proximal end of the pouch for cinching the pouch to a cinched configuration. The pouch may taper towards the closed distal end thereof when the pouch is in the second configuration.

An aspect of the instant disclosure provides a method for removing tissue from a body of a patient. Initially, an outer shaft of a specimen retrieval device is inserted within a body cavity of a patient. Thereafter, an inner shaft of the specimen retrieval device is deployed from the outer shaft to move a pouch of the specimen retrieval device from a first configuration to a second configuration. Subsequently, at least one tissue engaging device provided on the inner shaft is positioned towards a proximal end of the pouch for engaging tissue. Then, tissue of interest is engaged. Next, the tissue engaging device is positioned towards a distal end of the pouch for pulling tissue into the pouch. Subsequently, the pouch is removed from the body cavity of the patient.

Prior to removing the pouch, the open end of the pouch may be cinched. Prior to inserting the outer shaft of the specimen retrieval device, an access port may be positioned on tissue of the patient.

The inner shaft of the specimen retrieval device may be provided with at least one channel that is configured to receive the at least one tissue engaging device therein. Moreover, the inner shaft of the specimen retrieval device may be provided with at least one spring that is configured to couple to the pouch. A pair of jaw members, a needle, a barbed suture or a suction device may be utilized for the at least one tissue engaging device.

BRIEF DESCRIPTION OF THE DRAWINGS

Embodiments of the presently disclosed specimen retrieval device are described hereinbelow with reference to the drawings wherein.

DETAILED DESCRIPTION OF THE EMBODIMENTS

Figure 1:
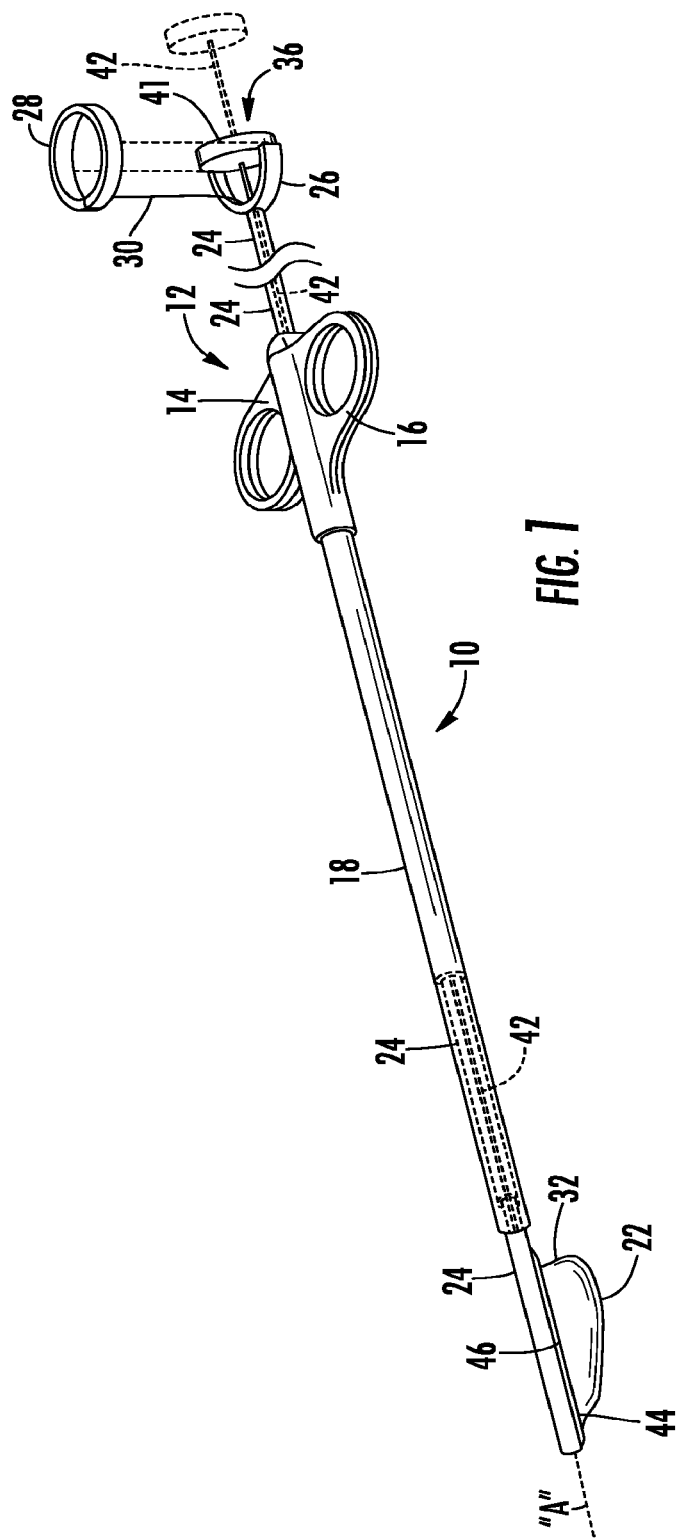
FIG. 1 is a side, perspective view of a specimen retrieval device according to an embodiment of the instant disclosure.

Embodiments of the present disclosure will now be described in detail with reference to the drawings, in which like reference numerals designate identical or corresponding elements in each of the several views. As used herein, the term distal refers to the portion of the instrument which is farthest from the user, while the term proximal refers to that portion of the instrument which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures.

Figure 2:
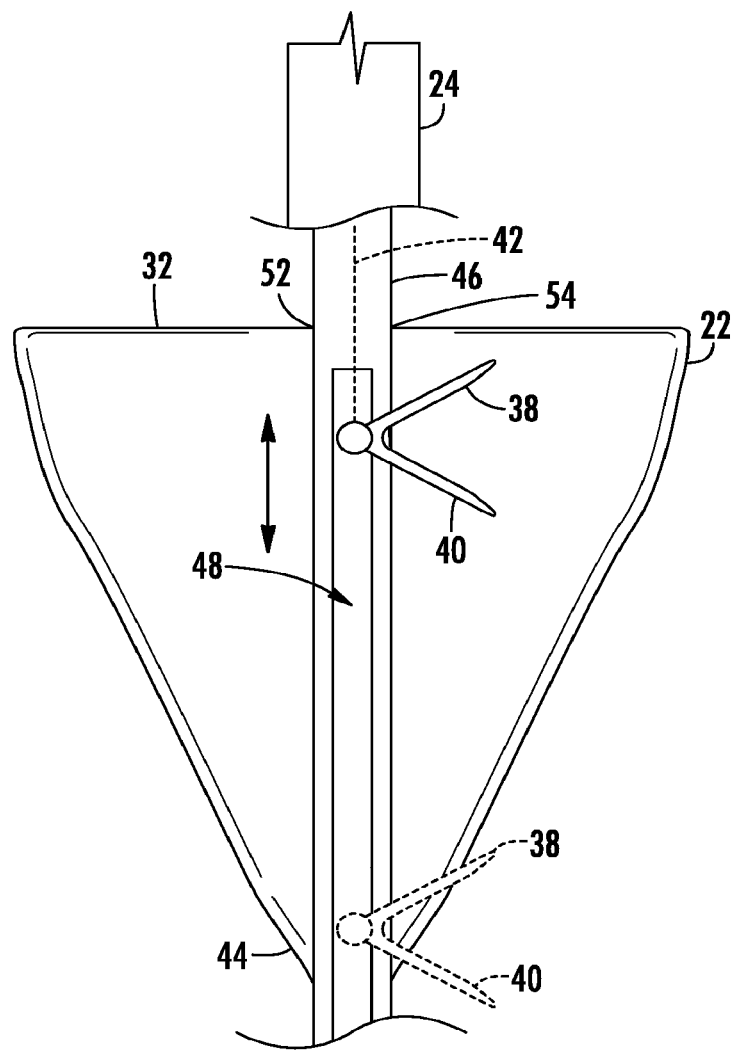
FIG. 2 is a partial, side view of a distal end of an inner shaft of the specimen retrieval device shown in FIG. 1 illustrating components of the distal end.
Figure 3:
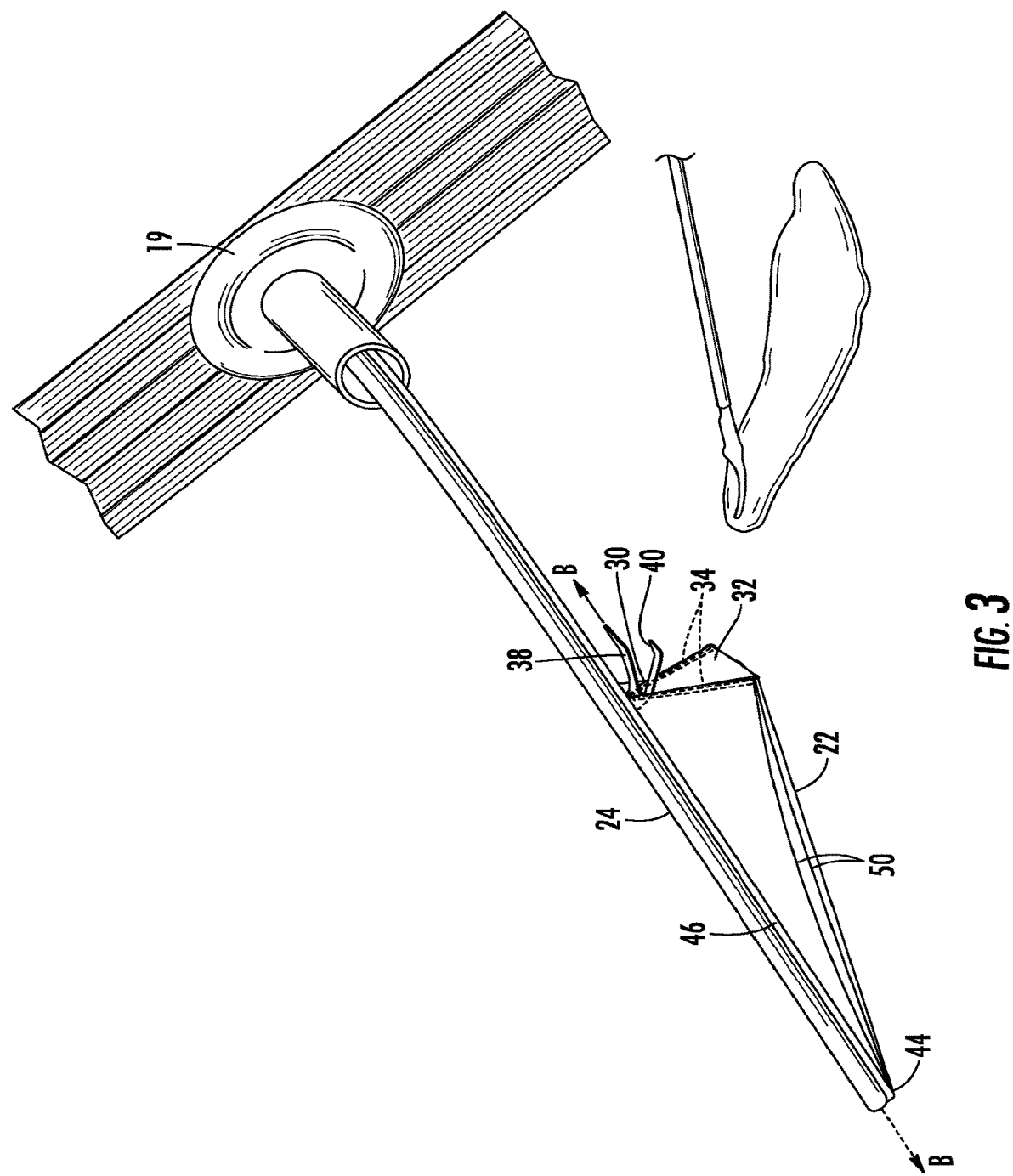
FIG. 3 is a perspective view of the inner shaft and a pouch of the specimen retrieval device shown in FIG. 1 positioned within a body cavity through an access port, wherein the pouch is in an open configuration for receiving tissue.
Figure 4:
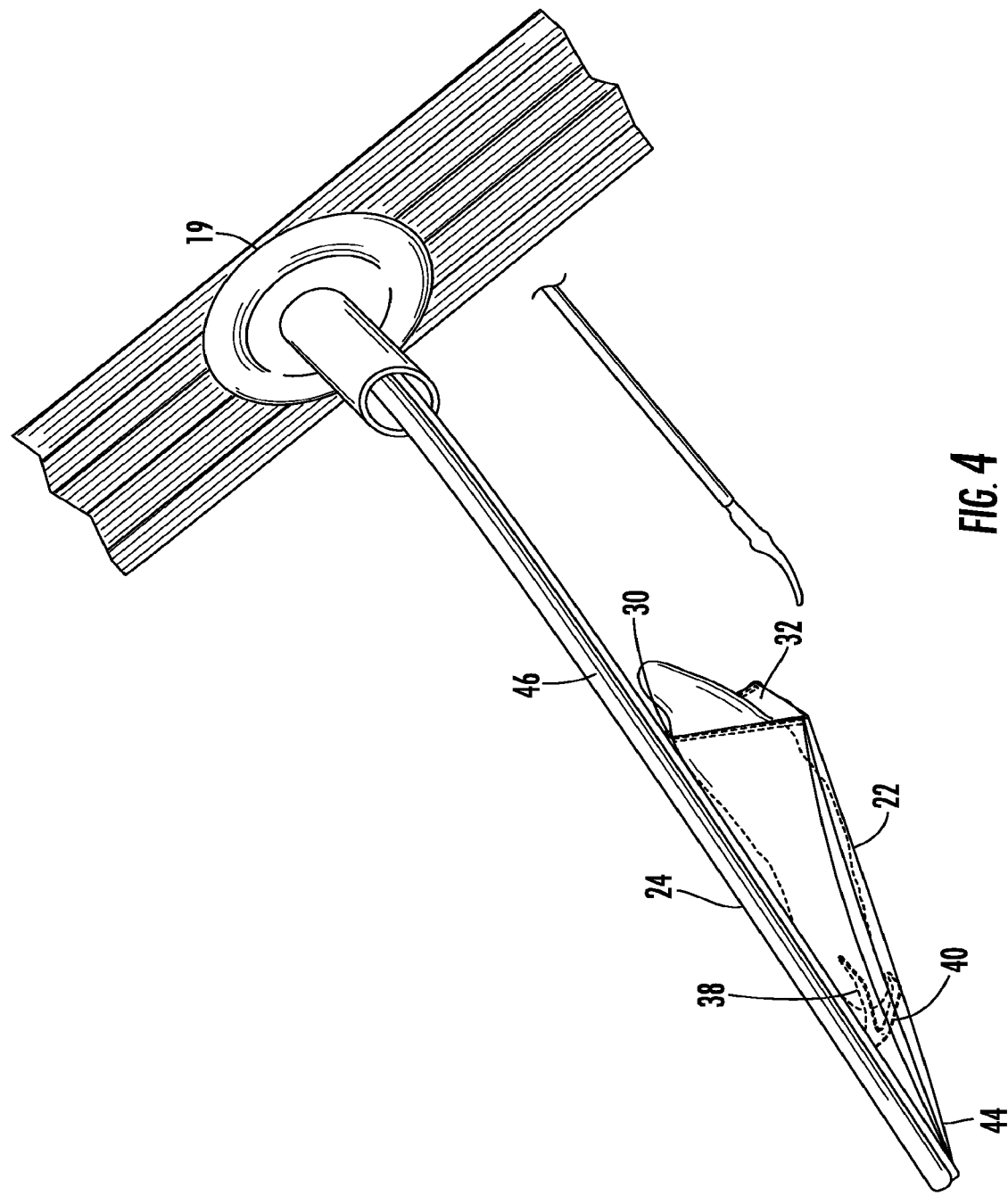
FIG. 4 is a perspective view of the inner shaft and pouch shown in FIG. 3 with tissue positioned within the pouch.
Figure 5:
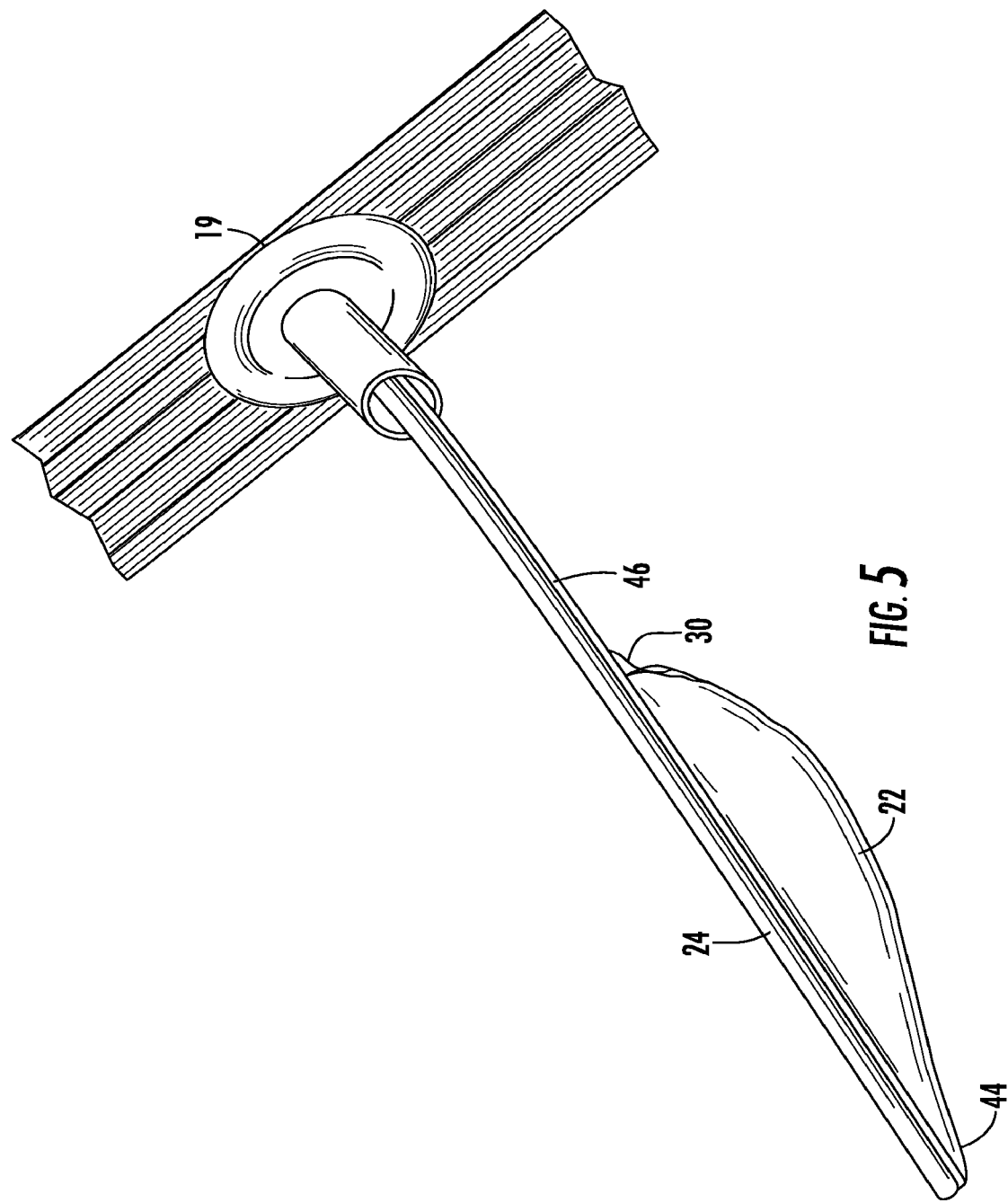
FIG. 5 is a perspective view of the inner shaft and pouch shown in FIGS. 3-4 with tissue positioned within the pouch and the pouch in a cinched configuration.

With reference to FIGS. 1-5, and initially with reference to FIG. 1, a specimen retrieval device 10 according to an embodiment of the present disclosure is illustrated. Briefly, specimen retrieval device 10 includes a housing 12 that includes handle portions 14 and 16 (FIG. 1) that are fixedly joined together. An elongated tube or outer shaft 18 extends from the housing 12 and is dimensioned for insertion through a trocar cannula or access port 19 (FIG. 3) for endoscopic or laparoscopic procedures. In certain embodiments, the outer shaft 18 may be configured to articulate. A longitudinal axis "A-A" is defined through the outer shaft 18 and is oriented in a substantially parallel direction with respect to a longitudinal axis "B-B" that is defined through a pouch 22 when the pouch 22 is in the deployed state (FIGS. 3-5).

An inner shaft 24 that extends within and along a length of the outer shaft 18 operably couples to a grasping member 26 (FIG. 1). Grasping member 26 is configured for engagement by a user's fingers and is configured to translate or move the inner shaft 24 within the outer shaft 18.

A pull ring 28 is operably coupled to a proximal end of a cinch 30 (e.g., a suture "S," thread, wire, cable or the like) by any suitable coupling method, e.g., tied, adhesive, etc., and is configured to facilitate pulling the cinch 30 proximally through the inner shaft 24. In the illustrated embodiment, pull ring 28 releasably couples, via one or more suitable coupling methods, e.g., a press or friction fit, to the grasping member 26. A distal end of the cinch 30 operably coupled to a portion, e.g., an open proximal portion 32 (FIGS. 3-4), of the pouch 22.

A deformable spring 34 (shown in phantom in FIG. 3) operably couples to the inner shaft 24 via one or more suitable coupling methods (e.g., the spring 34 may be overmolded to the inner shaft 16) and includes two generally flexible or resilient strips 35a, 35b (shown in phantom in FIG. 3) that move from a stressed or non-expanded state (FIG. 5) to an unstressed or freely expanded state (FIGS. 3-4) when the pouch 22 is deployed from the outer shaft 18. In the stressed or non-expanded state, the pouch 22 is wound or wrapped around the resilient strips of the inner shaft 24. Wrapping the pouch 22 around the resilient strips facilitates deploying the pouch 22 from the relatively small area within the outer shaft 18. In an unstressed or freely expanded condition, the two resilient strips collectively form a generally circumferential or triangular configuration for supporting a periphery of the open proximal portion 32 of the pouch 22 (see FIGS. 3-4 for example).

For a more detailed description of the specimen retrieval device 10 and operative components associated therewith, reference is made to commonly-owned U.S. Pat. No. 5,647,372 to Tovey et al., filed on Sep. 16, 1994, the entirety of which being incorporated herein by reference.

With reference again to FIG. 1, and with reference to FIG. 2, inner shaft 24 includes an actuation device 36 that is configured to control operation of a tissue engaging device, e.g., a pair of jaw members 38, 40 (FIG. 2). To this end, actuation device 36 includes a base portion 41 that may be configured for grasping by a user and a flexible rod 42 (or other suitable device, e.g., a wire). Base portion 41 releasably couples, via one or more suitable coupling methods, e.g., a press or friction fit, to the grasping member 26. Rod 42 includes a proximal end that couples to a distal end of the base 41 and extends distally from the base portion 41. A distal end of the rod 42 is positioned through an aperture (not explicitly shown) provided at a proximal end of the grasping member 26. The distal end of the rod 42 extends from the grasping member 26 to a rail 46 disposed on the inner shaft 24 and couples to the jaw members 38, 40 by suitable coupling methods (FIG. 2).

Continuing with reference to FIG. 2, in accordance with the instant disclosure, proximal and distal movement of the actuation device 36 moves the jaw members 38, 40 proximally and distally within the pouch 22 along the inner shaft 24. Actuation device 36 is configured such that as the base portion 41 of the actuation device 36 is moved proximally, the jaw members 38, 40 move towards the open proximal portion 32 and automatically to an open configuration (FIGS. 2-3). Likewise, as the base portion 41 of the actuation device 36 is moved distally, the jaw members 38, 40 move towards a closed distal portion 44 of the pouch 22 and automatically to a closed configuration (see FIGS. 2 and 4-5). A spring or other suitable device (not shown) may be coupled to the jaw members 38, 40 to bias the jaw members to the open or closed configuration.

Alternatively, in an embodiment, a cam member (not shown) may be positioned on the jaw members 38, 40 and to move the jaw members 38, 40 between the open and closed configurations. In this particular embodiment, rotation of the base 41 of the actuation device 36 in a first direction may actuate the cam member to cam the jaw members 38, 40 to the closed configuration and rotation of the base 41 in a second direction may actuate the cam member to cam the jaw members 38, 40 to the open configuration. Those skilled in the art will appreciate other methods and/or devices that may be utilized to move the jaw members 38, 40 between the open and closed configuration.

In the illustrated embodiment, a channel 48 is provided at the distal end of the rail 46 and extends at least partially along a length thereof 46 (FIG. 2). In an embodiment, such as the illustrated embodiment, the channel 48 extends along the inner shaft and is positioned to abut the pouch 22. Specifically, the channel 48 extends along the rail 46 and abuts the open proximal portion 32 and the closed distal portion 44 of the pouch 22. As can be appreciated, by not allowing the channel 48 to extend proximally past the open upper portion 32 helps to ensure that the jaw members 38, 40 (and excised tissue grasped therebetween) do not extend beyond the confines of the pouch 22, which, in turn, helps to ensure that the excised tissue does not migrate from the pouch 22.

Pouch 22 may be made from any suitable biocompatible materials (e.g., nylon) capable of forming an impermeable flexible membrane. Pouch 22 includes a generally tubular or elongated configuration that is defined by the openable and closable proximal portion 32 and closed distal portion 44. A channel of suitable configuration extends along the pouch 22 and includes a portion of the cinch 30 therein that is utilized to cinch the pouch 22 after tissue is positioned within the pouch 22. Moreover, proximal portion 32 includes a sleeve (not explicitly shown) that is configured to receive the resilient members of the spring 34. The sleeve may be formed on pouch 22 via folding the proximal portion 32 into an interior of the pouch 22 and, subsequently, gluing the proximal portion 32 thereto. Alternatively, in embodiments, the spring 34 may not be utilized and the proximal portion 32 of the pouch 22 may be formed from a compressible material that allows the proximal portion 32 of the pouch 22 to move between a compressed condition to a non-compressed condition. In the non-compressed condition, proximal portion 32 defines an opening that is configured to allow a clinician to position tissue of interest within the pouch 22. Moreover, in the non-compressed condition, the pouch 22 may taper towards the closed distal end 44 thereof when the pouch 22. Alternatively, the pouch 22 may not taper towards the closed distal end 44 thereof when the pouch 22.

A pair of sidewalls 52, 54 of the pouch 22 are coupled to the rail 46 adjacent the channel 48 of the rail by suitable coupling methods (FIG. 2). Each of the sidewalls 52, 54 abuts a corresponding side of the channel 48 to allow unobstructed movement of the jaw members 38, 40 within the pouch 22.

With reference to FIGS. 3-5, operation of the specimen retrieval device 10 is now described. In use, the access port 19 may be positioned on a patient to allow access of the specimen retrieval device 10 into a body cavity of a patient (FIG. 3). Thereafter, inner shaft 24 may be deployed from the outer shaft 18 and the outer shaft 18 may be removed from the body cavity of the patient while the inner shaft 24 is kept within the body cavity. As can be appreciated, after deployment of the inner shaft 24, the outer shaft 18 may also be kept within the body cavity. Once the inner shaft 24 is deployed from the outer shaft 18, the openable proximal end 32 of the pouch 22 is forced to the open configuration via the biasing force of the resilient members of the spring 30 (FIG. 3).

In the open configuration, the jaw members 38, 40 may be moved towards the open proximal end 32 of the pouch 22. In this position, the jaw members 38, 40 are in the open configuration and set to grasp excised tissue. In embodiments, such as the illustrated embodiment, a surgeon may grasp the excised tissue with a separate implement (e.g., graspers) and position the excised tissue between the jaw members 38, 40. Alternatively, a surgeon may move the pouch 22 including the jaw members 38, 40 adjacent excised tissue and grasp the excised tissue with the jaw members 38, 40.

Once tissue is positioned between the jaw members 38, 40 the base portion 41 of the actuation device may be moved distally, which, in turn, moves the jaw members 38, 40 along the channel 48 of the rail 46 toward the closed distal portion 44 of the pouch 22 and to the closed configuration (FIG. 4).

A surgeon may then pull the pull ring 28 proximally which cinches the pouch 22 (FIG. 5). Thereafter, the inner shaft 24 including the cinched pouch 22 may be removed from the body cavity of the patient through access port 19.

The specimen retrieval device 10 of the present disclosure allows a user to insert excised tissue (e.g., relatively large samples of excised tissue) within the pouch 22 while maintaining the compactness (e.g., unfolded configuration) of the pouch 22. Moreover, because the excised tissue is pulled into the pouch 22, the likelihood of the excised tissue bunching up when being positioned inside the pouch is reduced, if not eliminated, which, in turn, may make it easier to retrieve the pouch 22 through the usually a small laparoscopic incision or access port 19.

Figure 6A:
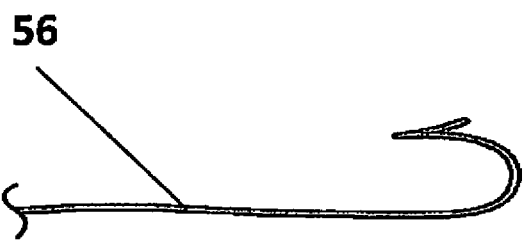
FIGS. 6A-6C are sides views illustrating various tissue engaging devices that may be utilized with the specimen retrieval device shown in FIG. 1.
Figure 6B:
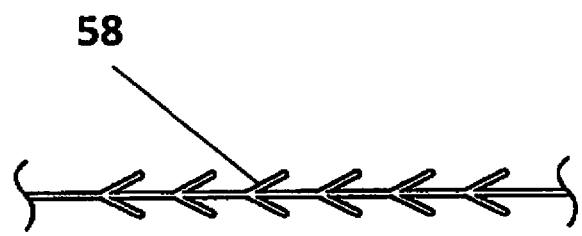
Figure 6C:
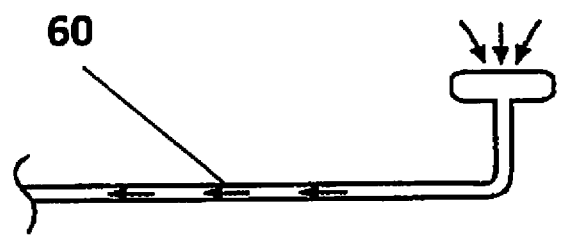

From the foregoing and with reference to the various figure drawings, those skilled in the art will appreciate that certain modifications can also be made to the present disclosure without departing from the scope of the same. For example, while the jaw members 38, 40 have been described herein as being utilized as the tissue engaging device, other tissue engaging devices may also be utilized. For example, any type of needle 56 (FIG. 6A), a barbed suture 58 (FIG. 6B), a suction device 60 (FIG. 6C) or other suitable device may be utilized in place of the jaw members 38, 40. As can be appreciated, certain modifications may need to be made to specimen retrieval device 10 to accommodate the different tissue engaging devices implemented.

In embodiments, one or more support members 50 (see FIG. 3 for example) may be provided along a surface of the pouch 22 and may be configured to facilitate moving the pouch 22 to the open configuration. For example, a resilient bar, wire or the like may extend along the surface of the pouch 22 that is provided opposite the side walls 52, 54 of the pouch 22. In this particular embodiment, the bar and/or wire may be woven or other attached to an interior or exterior of the pouch 22.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval device comprising:
a handle portion;
an outer shaft extending from the handle portion;
an inner shaft having a proximal portion, a distal portion and an outer surface, the inner shaft extending from the handle portion within the outer shaft;
a pouch supported on the distal portion of the inner shaft, the pouch having an open proximal end and a closed distal end;
a tissue engaging device supported on the inner shaft, the tissue engaging device being movable along the outer surface of the inner shaft from a position outside of the pouch through the open proximal end of the pouch to a position located within the pouch; and
a rail disposed on the inner shaft, the tissue engaging device being movable along the rail and the inner shaft, the rail defining a channel that extends between the open and closed ends of the pouch, the tissue engaging device being movable along the channel of the rail, wherein the tissue engaging device is configured to engage tissue and move the tissue through the open proximal end of the pouch while the open proximal end of the pouch is positioned proximally of the closed distal end of the pouch.

2. The specimen retrieval device of claim 1, wherein the open end of the pouch is supported at a position proximally of the closed end of the pouch.

3. The specimen retrieval device of claim 1, wherein the closed end of the pouch is supported adjacent a distal end of the inner shaft.

4. The specimen retrieval device of claim 1, wherein the pouch is tubular.

5. The specimen retrieval device of claim 1, wherein the tissue engaging device includes a pair of jaw members.

6. The specimen retrieval device of claim 1, wherein the pouch interfaces with a spring, the spring being configured to open the open end of the pouch.

7. The specimen retrieval device of claim 1, wherein the specimen retrieval device includes a cinch for cinching the pouch to a cinched configuration.

8. The specimen retrieval device of claim 2, wherein the pouch tapers from the open end towards the closed end.

9. A specimen retrieval device comprising:
a handle portion;
an inner shaft having a proximal portion extending from the handle portion, a distal portion, and an outer surface;
a pouch supported on the distal portion of the inner shaft, the pouch having an open proximal end and a closed distal end;
a tissue engaging device supported on the inner shaft, an inner member extending along the inner shaft, the tissue engaging device movable along the inner member from a position outside of the pouch through the open proximal end of the pouch to a position located within the pouch, wherein the tissue engaging device is configured to engage tissue and move the tissue through the open proximal end of the pouch while the open proximal end of the pouch is positioned proximally of the closed distal end of the pouch, and
an actuation device having a proximal end extending through the handle portion and a distal end coupled to the tissue engaging device, the actuation device being movable within the inner shaft to control operation of the tissue engaging device.

10. The specimen retrieval device of claim 9, wherein the inner member includes a rail disposed within the inner shaft, the tissue engaging device being movable along the rail and the inner shaft.

11. The specimen retrieval device of claim 9, wherein the closed distal end of the pouch is supported adjacent a distal end of the inner shaft.

12. The specimen retrieval device of claim 9, wherein the pouch is tubular.

13. The specimen retrieval device of claim 9, wherein the tissue engaging device includes a pair of jaw members.

14. The specimen retrieval device of claim 9, wherein the pouch interfaces with a spring, the spring being configured to open the open proximal end of the pouch.

15. The specimen retrieval device of claim 9, wherein the specimen retrieval device includes a cinch for cinching the pouch to a cinched configuration.

16. The specimen retrieval device of claim 9, wherein the pouch tapers from the open proximal end towards the closed distal end.

17. The specimen retrieval device of claim 9, wherein the specimen retrieval device further includes an outer shaft extending from the handle portion.

18. The specimen retrieval device of claim 17, wherein the inner shaft extends within the outer shaft.

* * * * *